United States Patent [19]

Chwalisz et al.

[11] Patent Number: 5,719,136
[45] Date of Patent: Feb. 17, 1998

[54] COMBINATION OF PROGESTERONE ANTAGONISTS AND ANTIESTROGENS WITH PARTIAL AGONISTIC ACTION FOR HORMONE SUBSTITUTION THERAPY FOR PERIMENOPAUSAL AND POSTMENOPAUSAL WOMEN

[75] Inventors: Kristof Chwalisz; Klaus Stöckemann, both of Berlin, Germany

[73] Assignee: Schering Aktiengesellschaft, Berlin, Germany

[21] Appl. No.: 628,702

[22] PCT Filed: Oct. 17, 1994

[86] PCT No.: PCT/EP94/03408

§ 371 Date: Jul. 5, 1996

§ 102(e) Date: Jul. 5, 1996

[87] PCT Pub. No.: WO95/11013

PCT Pub. Date: Apr. 27, 1995

[30] Foreign Application Priority Data

Oct. 17, 1993 [DE] Germany .................. 43 35 876.4

[51] Int. Cl.$^6$ .................................. A61K 31/565
[52] U.S. Cl. .................. 514/170; 514/171; 514/179; 514/324; 514/428; 514/648
[58] Field of Search .................. 514/170, 179, 514/324, 428, 648, 171

[56] References Cited

FOREIGN PATENT DOCUMENTS 178 862   4/1986   European Pat. Off. .
93/17686  9/1993   WIPO .

OTHER PUBLICATIONS

RN 96346-61-1 (Onapristone), 1992.

*Primary Examiner*—Rebecca Cook
*Attorney, Agent, or Firm*—Millen, White, Zelano, & Branigan, P.C.

[57] ABSTRACT

This invention describes the use of at least one compound having a progesterone-antagonistic (PA) action and at least one compound having an antiestrogenic (AÖ) action with a simultaneous partial agonistic action for the production of pharmaceutical agents for hormone substitution therapy (HRT) for perimenopausal and postmenopausal women.

In the case of combined use of progesterone antagonist and antiestrogen, the stimulation of the endometrium by the progesterone antagonist that is caused by its partial agonistic action when an antiestrogen is used by itself is inhibited.

For example, a pharmaceutical agent according to the invention contains onapristone (progesterone antagonist) and tamoxifen (antiestrogen).

4 Claims, No Drawings

COMBINATION OF PROGESTERONE ANTAGONISTS AND ANTIESTROGENS WITH PARTIAL AGONISTIC ACTION FOR HORMONE SUBSTITUTION THERAPY FOR PERIMENOPAUSAL AND POSTMENOPAUSAL WOMEN

This is a 371 of PCT/EP94/03408 Oct. 17, 1994.

This invention relates to the use of at least one compound having a progesterone-antagonistic (PA) action, as well as at least one compound having an antiestrogenic (AÖ) action with a simultaneous partial agonistic action for the production of pharmaceutical agents for hormone substitution therapy for perimenopausal and postmenopausal women.

Upon entering menopause (climacteric period), so-called climacteric symptoms occur in women owing to altered hormone production. Because of the reduced estrogen production, the risk of osteoporosis (reduction of bone tissue while leaving the bone structure intact, due to increased bone degradation and/or reduced bone accretion) increases at the same time; also, in the case of postmenopausal women, a myocardial infarction rate that is considerably higher than that for premenopausal women, as well as a higher occurrence of other cardiovascular diseases are observed, which is also attributed to reduced estrogen production.

Hormone substitution therapy (hormone replacement therapy=HRT) with estrogens or with an estrogen/gestagen combination has been the standard method to date for treating the symptoms associated with menopause (Ernster VL et al. (1988): Benefits and Risks of Menopausal Estrogen and/or Progestin Hormone Use; Prev. Med. 17:201–223).

Estrogen exerts a protective action on the cardiovascular system, the bones (reduction of the risk of osteoporosis), and the central nervous system (avoidance of so-called "hot flushes"). In contrast, the long-term use of estrogens in hormone replacement therapy leads to an increased risk of developing an endometrial carcinoma (Ernster VL et al. (1988): Benefits and Risks of Menopausal Estrogen and/or Progestin Hormone Use; Prev. Med. 17:201–223).

The stimulating effect of estrogen on the endometrium is suppressed by the simultaneous use of a gestagen for hormone substitution therapy (Gibbson WE, 1986, Biochemical and Histologic Effects of Sequential Estrogen/Progestin Therapy on the Endometrium of Postmenopausal Women; Am. J. Obstet. Gynecol: 154:46–61); however, when combined therapy with an estrogen and gestagen is administered, the protective effects of the estrogenic components with respect to the plasma lipids are at least diminished (Lobo R. (1992): The Role of Progestins in Hormone Replacement Therapy; Am. J. Obstet. Gynecol. 166: 1997–2004).

In addition, because of the hormone dosage, which is reduced in comparison with an oral contraceptive agent, undesirable intracyclic menstrual bleeding occurs with estrogen/gestagen treatment (Hillard TC et al. (1992): Continuous Combined Conjugated Equine Estrogen-Progestagen Therapy: Effects of Medroxyprogesterone Acetate and Norethindrone Acetate on Bleeding Patterns and Endometrial Histologic Diagnosis; A. J. Obstet. Gynecol. 167: 1–7).

Finally, more recent findings show that some gestagens increase the risk of the development of breast cancer disease (Staffa J. A. et al. (1992): Progestins and Breast Cancer: An Epidemiologic Review; 57: 473–491); King R. J. B. (1991): A Discussion of the Roles of Estrogen and Progestin in Human Mammary Carcinogenesis; J. Ster. Biochem. Molec. Bio. 39: 8111–8118).

In summary, the picture arises that the known estrogen monotherapies as well as estrogen/gestagen combination therapies do not provide any satisfactory options for treating the symptoms associated with menopause.

Recently, the use of "true" antiestrogens for the production of pharmaceutical agents for hormone replacement therapy (HRT) has also been proposed (EP-A-0 178 862). "True" antiestrogens, according to EP-A-0 178 862, for example, are defined as tamoxifen, nafoxiden, MER-25, i.e., those antiestrogens that have a receptor-mediated effect and that simultaneously also have a partial estrogenic (agonistic) action.

A drawback to such a pharmaceutical agent that contains a "true" antiestrogen with partial estrogenic action is that because of the long-term estrogenic stimulation of the endometrium, as when estrogens are used, a higher risk of the development of an endometrium carcinoma exists (Fornander T. et al. (1989): Adjuvant Tamoxifen in Early Breast Cancer: Occurrence of New Primary Cancers; Lancet 21: 117–119).

In contrast, positive effects on the bones are noted from the partial estrogenic action of tamoxifen: in women, tamoxifen seems to partially prevent the degradation of the bone mass (Love R. R. et al. (1992): Effects of Tamoxifen on Bone Mineral Density in Postmenopausal Women with Breast Cancer; N. Engl. J. Med. 26:852–856).

In addition, studies with tamoxifen have shown that its antiestrogenic component is responsible for growth inhibition when used to treat breast carcinoma in postmenopausal women (Buckley M. M. T. et al. (1989); Tamoxifen: A Reappraisal of its Pharmacodynamic and Pharmacokinetic Properties and Therapeutic Use; Drugs 37: 451–490).

Accordingly, the necessary long-term use of an antiestrogen having a partial agonistic action in hormone substitution therapy is considered worrisome since stimulation of the endometrium can promote the development of an endometrial carcinoma.

The object of this invention is therefore to provide a pharmaceutical agent for hormone substitution therapy (HRT), which prevents the undesirable actions in the case of a long-term monotherapy with antiestrogens having a partial agonistic action (stimulation of the endometrium), but simultaneously leaves unaffected the protective effect on the bones and the cardiovascular system (based on the agonistic action) as well as the breast (antagonistic action), or which even intensifies the protective effects.

This object is achieved by this invention, namely by the use of at least one compound having a progesterone-antagonistic (PA) action, as well as at least one compound having an antiestrogenic (AÖ) action while also at the same time having a partial agonistic action for the production of such a pharmaceutical agent.

It has been found that in the pharmaceutical agent that is produced according to the invention, the components having a progesterone-antagonistic (PA) action inhibit the alterations (stimulation of the myometrium and endometrium) caused by the partial estrogenic action of the antiestrogen only in the uterus, but, surprisingly, the other effects that are greatly desired in hormone replacement therapy (for example in the bones and in the cardiovascular system) are retained.

The advantageous action that has been noted from the pharmaceutical agent that is produced according to the invention is brought about presumably in that the partial estrogenic action of the antiestrogen (Jordan V. C. et al. (1979): Effects of Estradiol Benzoate, Tamoxifen and Monohydroxytamoxifen on Immature Rat Uterine Progesterone Receptor Synthesis and Endometrial Cell Division; J. Steroid. Biochem. 11:285–291) is inhibited by the antiproliferative effect of the competitive progesterone antagonist (PA) (Wolf J. P. et al. (1989): Noncompetitive Antiestrogenic Effect of RU 486 in Blocking the Estrogen-Stimulated Luteinizing Hormone Surge and the Proliferative Action of Estradiol on Endometrium in Castrate Monkeys; Fertil. Steril. 52: 1055–1060; Chwalisz K. et al. (1992): Evaluation of the Antiproliferative Actions of the Progesterone Antagonists Mifepristone (RU 486) and onapristone (ZK 98 299) on Primate Endometrium; Society of Gynecologic Investigation, 39th Annual Meeting, San Antonio, Tex., Abstract). The progesterone antagonist selectively exerts a protective function on the endometrium.

It has been shown that in ovariectomized rats (as an animal model for the postmenopausal woman), the proliferation of the myometrium or endometrium that is stimulated by estradiol is inhibited by competitive progesterone antagonists. But here mainly the stromal or myometrial areas are affected; the luminar epithelium is less affected. When an antiestrogen having a partial estrogenic action (e.g., tamoxifen) is combined with a competitive progesterone antagonist (PA) (onapristone), it has now been found that both the myometrial areas and the stromal and epithelial areas in the uterus are inhibited.

The pharmaceutical agents that are produced according to the invention are thus suitable for preventive use and for curative use in hormone substitution therapy (HRT), since degradation of the bone material is prevented by the partial estrogenic action of the antiestrogen; the estrogenic component simultaneously exerts a protective action on the cardiovascular system, and the undesirable stimulating effect on the endometrium is prevented by the antiproliferative action of the competitive progesterone antagonist, for the purpose of ensuring a protective function.

These pharmaceutical agents are thus suitable for long-term use in HRT and can be used with continuous or intermittent administration.

The fact that progesterone-antagonistically effective compounds in combination with antiestrogenically effective compounds can be used for the production of pharmaceutical agents for inducing labor, for terminating pregnancy, and for treating gynecological disorders (dysmenorrhea and endometriosis) is already known from EP-A-0 310 541.

The ratio by weight of the two components in the new pharmaceutical agent can be varied within broad limits in this case. Thus, both the same amounts of progesterone antagonist and antiestrogen and an excess of one of the two components can be used. Progesterone antagonist and antiestrogen are used together, separately, simultaneously, and/ or sequentially, at a ratio by weight of basically 50:1 to 1:50, preferably 25:1 to 1:25, and especially 10:1 to 1:10. Simultaneous administration is preferred. In the case of sequential administration, the compound administered second can be added at any time after the administration of the compound that is given first, as long as it is also bioavailable to the patient simultaneously in the presence of an effective amount of the compound that is administered first. For example, the antiestrogen can be added starting on the second day after the administration of progesterone antagonist, and then both the progesterone antagonist and the antiestrogen can be administered starting with the third day.

Preferably, the progesterone antagonist and antiestrogen can be administered combined in one dosage unit.

In general, one-time daily administration of the two components is adequate.

The duration of the treatment with the pharmaceutical agent according to the invention is not limited timewise; long-term treatment can also be carried out intermittently, i.e., an extended period, during which the components are administered, is followed by a shorter pause in intake in each case; for example, the treatment may last for 3 to 6 months, followed by an approximately 2-month pause in intake.

As competitive progesterone antagonists, all compounds that competitively block the action of progesterone on the gestagen receptor (progesterone receptor) and in this process exhibit no specific gestagenic activity are suitable; this blocking can be accomplished by the administered substance itself or by its metabolites. For example, the following steroids are suitable:

11β-[(4-N,N-Dimethylamino)-phenyl]-17β-hydroxy-17α-propinyl-4,9(10)-estradien-3-one (RU-38486);

11β-[(4-N,N-dimethylamino)-phenyl]-17β-hydroxy-18-methyl-17α-propinyl-4,9(10)-estradien-3-one and 11β-[(4-N,N-dimethylamino)-phenyl]-17aβ-hydroxy-17aβ-propinyl-D-homo-4,9(10), 16-estratrine-3-one (all EP-A-0 057 115); also 11β-p-(methoxyphenyl-17β-hydroxy-17α-ethinyl-4,9 (10)- estradien-3-one (Steroids 37 (1981), 361–382);

11β-(4-acetylphenyl)-17β-hydroxy-17α-(prop-1-inyl)-4, 9(10)- estradien-3-one (EP-A0 190 759), as well as the 11β-aryl-14β-estradienes and 11β-aryl-14β-estratrienes, described in EP-A0 277 676, the 19,11β-bridged steroids, which are the object of EP-A0 283 428, the 11β-aryl-6-alkyl (or 6-alkenyl or 6-alkinyl)-estradienes and -pregnadienes known from EP-A0 289 073 and the 11β-aryl-7-methyl (or 7-ethyl)-estradienes known from EP-A0 321 010 as well as the 10β-H steroids of EP-A 0 404 283, for example, (Z)-11β-[4-(dimethylamino)phenyl]-17α-(3-hydroxyprop-1-enyl)-estr-4-en-17β-ol.

In addition, the following can be mentioned as typical representatives of competitive progesterone antagonists to be used according to the invention, for example:

11β-(4-Dimethylamino)-17α-hydroxy-17β-(3-hydroxypropyl)-13α-methyl-4,9-gonadien-3-one (EP-A 0 129 499);

11β-(4-acetylphenyl)-17β-hydroxy-17α-(3-hydroxyprop-1(Z)- enyl)-4,9(10) -estradien-3-one (EP-A 0 190 759);

11β,19-[4-(cyanophenyl)-o-phenylene]-17β-hydroxy-17α-(3-hydroxyprop-1(Z)-enyl)-4-androsten-3-one and 11β,19-[4-(3-pyridinyl)-o-phenylene]-17β-hydroxy-17α-(3-hydroxyprop-1(Z)-enyl)-4-androsten-3-one (both EP-A-0 283 428).

The list of progesterone antagonists is not exhaustive; also other competitive progesterone antagonists described in the above-mentioned publications, as well as those from publications not mentioned here are suitable.

The competitive progesterone antagonists can be administered, for example, locally, topically, enterally, transdermally, or parenterally.

For the preferred oral administration, tablets, coated tablets, capsules, pills, suspensions, or solutions that can be produced in the usual way with the additives and vehicles commonly used in galenicals are especially suitable. For local or topical use, for example, vaginal suppositories, vaginal gels, implants, vaginal rings, intrauterine release systems (IUDs), or transdermal systems such as skin patches are suitable.

A dosage unit contains about 0.25 to 50 mg of 11β-[(4-N,N-dimethylamino)-phenyl]-17α-hydroxy-17β-(3- hydroxypropyl)-13α-methyl-4,9(10)-gonadien-3-one or a biologically equivalent amount of another competitive progesterone antagonist.

If the administration of the pharmaceutical agent produced according to the invention is done by an implant, a vaginal ring, an IUD, or a transdermal system, these administration systems must be designed in such a way that the dose of the competitive progesterone antagonist that is released by them daily lies in this range of 0.25 to 50 mg.

As antiestrogens having a partial agonistic (estrogenic) action, all such commonly used antiestrogens are considered. They can be used in approximately the same amounts as the antiestrogens that are already commercially available, i.e., the daily dose is about 5–100 mg for tamoxifen or biologically equivalent amounts of another antiestrogen. The daily dose is always to be selected such that an atrophic state develops at the endometrium but the estrogen effects (substitution) on the bones and the cardiovascular system are maintained. Because of its high estrogen receptor concentration, the endometrium responds in a more sensitive way to estrogens or antiestrogens than other target organs. As antiestrogens, for example, the following can be mentioned:

| | |
|---|---|
| Tamoxifen = | (Z)-2-[p-(1,2-Diphenyl-1-butenyl)-phenoxy]-N,N-dimethylethylamine, |
| nafoxidine = | 1-2-[4-(6-methoxy-2-phenyl-3,4-dihydro-1-naphthyl)-phenoxy]-ethylpyrrolidine, hydrochloride, |
| Mer 25 = | 1-[p-(2-diethylaminoethoxy)-phenyl]-2-(p-methoxyphenyl)-1-phenylethanol, |
| raloxifen = | 6-hydroxy-2-(p-hydroxyphenyl)benzo-[b]thien-3-yl-p-(2-piperidino-ethoxy)phenylketone, hydrochloride; |

Compounds with progesterone-antagonistic action and an antiestrogenic action can be administered, e.g., locally, topically, enterally, or parenterally.

For the preferred enteral administration, especially tablets, coated tablets, capsules, pills, suspensions, or solutions that can be produced in the usual way with the additives and vehicles commonly used in galenicals are suitable. For local or topical use, for example, vaginal suppositories or transdermal systems such as skin patches are suitable.

An antiestrogen dosage unit contains 1–100 mg of tamoxifen or a biologically equivalent amount of another antiestrogenically effective compound.

The examples below are used for a more detailed explanation of this invention:

Example 1

| | |
|---|---|
| 10.0 mg | of 11β-[(4-N,N-dimethylamino)-phenyl]-17α-hydroxy-17β-(3-hydroxypropyl)-13α-methyl-4,9-gonadien-3-one |
| 140.5 mg | of lactose |
| 69.5 mg | of corn starch |
| 2.5 mg | of poly-N-vinylpyrrolidone |
| 2.0 mg | of aerosil |
| 0.5 mg | of magnesium stearate |
| 225.0 mg | total weight of the tablet |

Example 2

| | |
|---|---|
| 20.0 mg | of tamoxifen (antiestrogen having an agonistic partial action) |
| 50.0 mg | of 11β-[(4-N,N-dimethylamino)- |

-continued

| | |
|---|---|
| | phenyl]-17α-hydroxy-17β-(3-hydroxypropyl)-13α-methyl-4,9-gonadien-3-one |
| 105.0 mg | of lactose |
| 40.0 mg | of corn starch |
| 2.5 mg | of poly-N-vinylpyrrolidone 25 |
| 2.0 mg | of aerosil |
| 0.5 mg | of magnesium stearate |
| 220.0 mg | total weight of the tablet, which is produced in the usual way in a tablet press. Optionally, the active ingredients according to the invention can also be pressed separately into a two-layer tablet with respectively half of the above-indicated additives. |

Example 3

| | |
|---|---|
| 10.0 mg | of raloxifen |
| 30.0 mg | of 11β-[(4-N,N-dimethylamino)-phenyl]-17α-hydroxy-17β-(3-hydroxypropyl)-13α-methyl-4,9-gonadien-3-one |
| 125.0 mg | of lactose |
| 50.0 mg | of corn starch |
| 2.5 mg | of poly-N-vinylpyrrolidone 25 |
| 2.0 mg | of aerosil |
| 0.5 mg | of magnesium stearate |
| 220.0 mg | total weight of the tablet, which is produced in the usual way in a tablet press. Optionally, the active ingredients according to the invention can also be pressed separately into a two-layer tablet with respectively half of the above-indicated additives. |

Example 4

Composition of an oily solution:

| | |
|---|---|
| 100.0 mg | of tamoxifen |
| 343.4 mg | of castor oil |
| 608.6 mg | of benzyl benzoate |
| 1052.0 mg | = 1 ml |
| | The solution is loaded into an ampoule. |

Pharmacological Observations The tests were carried out on ovariectomized (ovx) rats (n=10 animals/group) (Gr. 1 to Gr. 6). The ovariectomized animals were treated s.c. for 3 to 8 days with estradiol+onapristone (0.3 μg+10.0 mg/day/animal) or with the antiestrogen tamoxifen (0.2 mg/day/animal)+onapristone (10.0 mg/day/animal). At the end of the test, the uteri were weighed and a routine histological opinion was rendered.

Results

The treatment with estradiol by itself results in a stimulation of the myometrium, the stromal and epithelial tissue in the uterus (Gr. 2). Simultaneous administration of the competitive progesterone antagonist onapristone causes the effects to be inhibited for the most part on the myometrium or stroma, while those on the epithelium are partially inhibited (Gr. 4). Onapristone by itself does not have any effect on the uterine tissue (Gr. 3). Treating ovariectomized rats with tamoxifen by itself (antiestrogen with partial estrogenic action) results, like the treatment with estradiol, in stimulation of various uterine tissue components and of the uterus weight (Gr. 5). By combining it with a competitive progesterone antagonist (onapristone), the stimulating effect of tamoxifen on the endometrium (stroma and epithelium) can be canceled out (Gr. 6).

TABLE 1

Morphological Changes in the Uterus

| Gr. 1 | Substance | Myome-trium | Endometrium Stróma | Epithelium | Weight of the uterus |
|---|---|---|---|---|---|
| 1 | ovx + vehicle | − | − | − | − |
| 2 | ovx + estradiol | +++ | +++ | +++ | +++ |
| 3 | ovx + onapristone | − | − | − | − |
| 4 | ovx + estradiol + onapristone | + | + | ++ | + |
| 5 | ovx + tamoxifen | ++ | ++ | ++ | ++ |
| 6 | ovx + tamoxifen + onapristone | + | − | − | + |

+ = stimulation   − = inhibition

We claim:

1. A method of providing hormone substitution therapy (HRT) to a perimenopausal or postmenopausal woman, comprising administering to a patient in need of such treatment effective amounts of a compound having progesterone-antagonistic (PA) activity and a compound simultaneously having antiestrogenic (AÖ) and partial agonistic activity.

2. A method of claim 1, wherein the PA is 11β-[(4-N,N-dimethylamino)-phenyl]-17β-hydroxy-17α-propinyl-4,9(10)-estradien-3-one or 11β-[(4-dimethylamino)-phenyl]-17α-hydroxy-17β-(3-hydroxypropyl)-13α-methyl-4,9-gonadien-3-one.

3. A method of claim 1, wherein the AÖ is (Z)-2-[p-(1,2-di-phenyl-1-butenyl)-phenoxy]-N,N-dimethylethylamine; 1-2-[4-(6-methoxy-2-phenyl-3,4-dihydro-1-naphthyl)-phenoxy]-ethyl-pyrrolidine, hydrochloride; 1-[p-(2-diethylaminoethoxy)-phenyl]-2-(p-methoxyphenyl)-1-phenylethanol; or 6-hydroxy-2-(p-hydroxyphenyl)-benzo[b]thien-3-yl-p-(2-piperidinoethoxy)phenylketone, hydrochloride.

4. A method of claim 1, wherein the PA is 11β-[(4-dimethylamino)-phenyl]-17α-hydroxy-17β-(3-hydroxypropyl)-13α-methyl-4,9-gonadien-3-one and the (AÖ) is (Z)-2-[p-(1,2-diphenyl-1-butenyl)-phenoxy]-N,N-dimethylethylamine.

* * * * *